United States Patent [19]

Lichtin et al.

[11] 4,451,342
[45] May 29, 1984

[54] LIGHT DRIVEN PHOTOCATALYTIC PROCESS

[75] Inventors: Norman N. Lichtin, Newton Center; Kalambella M. Vijayakumar, Allston, both of Mass.

[73] Assignee: Atlantic Richfield Company, Los Angeles, Calif.

[21] Appl. No.: 374,559

[22] Filed: May 3, 1982

[51] Int. Cl.$^3$ ............................................. B01J 19/12
[52] U.S. Cl. .......................... 204/157.1 R; 204/158 R; 204/162 R
[58] Field of Search ................... 204/157.1 R, 158 R, 204/162 R

[56] References Cited

U.S. PATENT DOCUMENTS 4,147,602 4/1979 Garbuny et al. ............. 204/157.1 R
4,177,120 12/1979 Zenty ........................... 204/157.1 R

FOREIGN PATENT DOCUMENTS 105625 8/1980 Japan ........................... 204/157.1 R Primary Examiner—Howard S. Williams
Attorney, Agent, or Firm—Roderick W. MacDonald

[57] ABSTRACT

A method for the light driven photocatalytic reduction of carbon dioxide or the bicarbonate ion to one or more compounds which comprises contacting certain metal compounds with the carbon dioxide and/or bicarbonate ion in the absence of separate physical electrolyte and electrodes, and conducting said contacting in the presence of a reducing agent such as water and light.

14 Claims, No Drawings

LIGHT DRIVEN PHOTOCATALYTIC PROCESS

BACKGROUND OF THE INVENTION

Heretofore, the photocatalytic reduction of carbon dioxide in the presence of water into various organic compounds such as formaldehyde and methanol has been accomplished using various chemical compounds such as titanium dioxide, tungsten trioxide, $Pb_3O_4$, iron oxide, calcium titanate, silicon carbide, and the like. See "Photoreduction of Carbon Dioxide and Water into Formaldehyde and Methanol on Semiconductor Materials" by Aurian-Blajeni, Halmann and Manassen, Solar Energy, Vol. 25, pp. 165-170, 1980. This photocatalytic process does not employ any physically separate electrodes or special electrolyte as does the classical electrolytic cell or photoelectrochemical cells as will be discussed in greater detail hereinafter. This photocatalytic process merely employs a catalytic material, preferably, dispersed in a carrier liquid for better carbon dioxide contacting purposes. The material to be reduced such as carbon dioxide, is brought into contact with the catalyst using light as a source of the energy of reduction.

Also heretofore, photoelectrochemical cells which employ two physically separate electrodes combined with a special electrolyte solution have been used to reduce carbon dioxide or the bicarbonate ion to organic compounds such as formaldehyde, methanol, and formic acid. These cells have employed silicon metal as one of the physically separate electrodes and carbon or the like as the counter electrode. In the operation of these cells at least part of the required energy of reduction is supplied by light energy, including solar radiation. See U.S. Pat. No. 4,219,392, issued Aug. 26, 1980 to Halmann.

BRIEF SUMMARY OF THE INVENTION

Accordingly, it was surprising to discover that certain compounds act as a catalyst in a light driven photocatalytic process for the reduction of carbon dioxide to certain compounds.

There is provided, according to this invention, a method for the light driven photocatalytic reduction of carbon dioxide or the bicarbonate ion to at least one compound which comprises contacting certain metal compounds or mixtures or combinations thereof with at least one of carbon dioxide and the bircarbonate ion in the presence of a reducing agent and light so that the energy of reduction is essentially supplied by said light.

This process distinguishes clearly over a photoelectrochemical process in that the process of this invention requires no physically separate electrodes or special electrolyte and is unexpected as can be seen from Example 2 hereinafter.

Accordingly, it is an object of this invention to provide a new and improved light driven photocatalytic method. It is another object to provide a new and improved method for a light driven photocatalytic reduction of carbon dioxide or the bicarbonate ion to other useful organic compounds. Other aspects, objects and advantages of this invention will be apparent to those skilled in the art from this disclosure and the appended claims.

DETAILED DESCRIPTION OF THE INVENTION

In accordance with this invention, carbon dioxide or the bicarbonate ion or a mixture of both are reduced to at least one compound selected from the group consisting of carbon monoxide, alcohols, aldehydes, hydrocarbons, and carboxylic acids, preferably each having from one to two carbon atoms per molecule, still more preferably carbon monoxide, formaldehyde, methane, methanol, and formic acid. The reduction is accomplished by contacting certain metal compounds with one or both of carbon dioxide and the bicarbonate ion and conducting such contacting in the presence of a reducing agent such as water and light so that the energy of reduction of the carbon dioxide and/or bicarbonate ion is essentially supplied by said light.

Thus, the useful compounds produced by the method of this invention are obtained without the use of an external electrical bias, special electrodes, or special electrolyte solutions.

The light employed can be sunlight or artificial light or a combination of both and can vary over a wide wavelength range so long as at least part of the incident light is of a wavelength that is absorbed by the metal compound employed. The time period for exposure to light can vary widely, there being no upper limit on the time of exposure from an operational point of view. The time limit for each exposure is dictated more by economics.

It has been found that without incident light no measurable reduction takes place, and that with light and no metal compound, no measurable reduction takes place, so that the combination of light and metal compound along with a reducing agent is necessary.

The metal compounds employed can be selected from the group consisting of CdSe, CoO, $Co_3O_4$, $Co_2O_3$, $Cr_2O_3$, $Cu_2O$, CuO, La-Ni-oxide, platinized La-Ni-oxide, $La_2O_3$, La-Ti-Oxide, $Nd_2O_3$, NiO, PbO, and mixtures and combinations thereof.

The metal compound or compounds are preferably employed in a subdivided form, for example, a powder, in order to expose a larger catalyst contacting surface to the carbon dioxide and/or bicarbonate ion. The extent of subdivision is not critical to the operability of the process, it being well within the skill of the art to determine whether coarse or fine particles or a combination thereof are to be employed in a particular application.

The metal compound or mixture or combination thereof is preferably dispersed in a carrier liquid to promote maximum contact between the metal compound and the material to be reduced. This carrier liquid is not employed as an electrolyte but is rather a physical suspension and mixing medium for the metal compound and carbon dioxide. The carrier helps provide maximum mixing and intimate contact between the materials in the presence of light. The carrier liquid is not critical as to its chemical composition, so long as it is chemically nondeleterious to the metal compound, the material to be reduced, and the reduction products. The carrier liquid can also serve as the reducing agent. Preferably, the carrier liquid is common water. The water may or may not have one or more chemical salts dissolved therein, but, unlike an electrolyte, the carrier need not have dissolved salts therein to any appreciable extent so far as the operation of this invention is concerned.

The amount of metal compound(s) and the amount and kind of reducing agent(s) employed in the process of this invention are not critical and can vary widely depending on economics and the like, the minimum criterion being only that an amount effective to obtain the desired reduction be present.

Other reducing agents that can be employed are hydrogen sulfide or organic waste materials such as sewage, vegetable matter or animal waste.

The metal compound can simply be exposed to the material to be reduced or, optionally, can first be heat treated to increase its activity when subsequently exposed to the compound or compounds to be reduced. If the metal compound is heat treated prior to contact with the material to be reduced, it is preferably heated at a temperature of from about 20° C. to about 600° C. for at least one hour. The heating can be carried out in air, an inert gas such as argon, or in a vacuum, and is preferably conducted for from about one hour to about forty-eight hours.

In the following Example 1, the metal compound was prepared by crushing to a fine powder in an agate mortar, the finest particles being removed by washing with water. The thus crushed and washed metal compound was dried and preconditioned by heating for twelve hours in argon at a temperature as indicated in Table I hereinafter.

In the examples, carbon dioxide was used as the material to be reduced. Purified grade carbon dioxide was deoxygenated by passage through a solution of chromous perchlorate stored over a zinc amalgam.

Deionized tap water was employed as the carrier liquid.

The carbon dioxide was dispersed through a sintered disc into 25 milliliters of water carrying approximately 0.1 grams of the subdivided metal compound dispersed therein. Bubbling of the carbon dioxide through this aqueous metal compound suspension provided adequate mixing. The carbon dioxide flow rate was 150 cubic centimeters per minute at 1 atmosphere. The aqueous metal compound suspension was contained in a pyrex reaction cell and a 150 watt Xenon lamp with quartz lenses was employed approximately 30 centimeters from the pyrex reaction cell to supply the incident light required for operation of the process.

Effluent gas from the reactor was passed through two traps immersed in, respectively, common ice and dry ice or traps containing distilled water which were immersed in common ice.

The contents of the reactor and the traps were analyzed after each run for methanol and formaldehyde. The methanol content was determined by gas chromatography on Poropak Q with helium as a carrier gas, flame ionization detection, and calibrated with external standards. Formaldehyde was determined by the standard chromotropic acid method.

EXAMPLE 1

Various metal compounds as set forth in Table I hereinafter were employed with a reaction time and temperature for all runs of approximately 30° C. and six hours.

TABLE I

| Run | Catalyst | Reported Band-Gap Energies eV | Pre-condition Temp./ °C. | 6-Hr. Yields η mole CH$_3$OH | CH$_2$O |
|---|---|---|---|---|---|
| 1 | CdSe | 1.8 | None | Trace | Trace |
| 2 | CdSe | 1.8 | 200 | Trace | 1.1 |
| 3 | CoO | 0.8 | 300 | 32.0 | 1.9 |
| 4 | Co$_3$O$_4$[a] | 0.9 | 300 | 17.5 | 3.7 |
| 5 | Co$_2$O$_3$ | — | 300 | 4.5 | 4.1 |
| 6 | Cr$_2$O$_3$ | 1.9 | 300–400 | 3.0 | 2.2 |
| 7 | Cu$_2$O | 1.9 | 100 | 9.6 | 4.2 |
| 8 | CuO | 1.4 | 300 | 9.5 | 3.9 |
| 9 | La—Ni—Oxide | ~0 | None | 17.3 | 2.4 |
| 10 | Platinized La—Ni—Oxide | ~0 | None | 30.0 | 4.3 |
| 11 | La$_2$O$_3$ | 2.6 | 400 | 5.0 | 6.8 |
| 12 | La—Ti—Oxide | ~0 | None | 14.0 | Trace |
| 13 | Nd$_2$O$_3$ | 2.2 | 400 | 12.2 | 5.4 |
| 14 | NiO | 1.95 | 300 | 2.7 | 8.2 |
| 15 | PbO | 3.2 | 300 | 7.6 | 2.2 |

[a] A minor amount of carbon monoxide product was detected by the NBS indicator method.

EXAMPLE 2

Silicon dioxide in the form of Ottawa sand was employed in the amount of 0.25 grams per milliliter of water using the procedure of Example 1 and a pretreatment of heating for twelve hours in argon at 100° C. After reaction for six hours at about 30° C., no methanol or formaldehyde was produced.

Reasonable variations and modifications are possible within the scope of this disclosure without departing from the spirit and scope of this invention.

We claim:

1. A method for the light driven photocatalytic reduction of carbon dioxide or the bicarbonate ion to at least one compound which comprises contacting at least one metal compound catalyst selected from the group consisting of of CoO, Co$_3$O$_4$, Co$_2$O$_3$, Cr$_2$O$_3$, Cu$_2$O, CuO, La-Ni-oxide, platinized La-Ni-oxide, La$_2$O$_3$, Nd$_2$O$_3$, NiO, PbO, and mixtures and combinations thereof with at least one of carbon dioxide and the bicarbonate ion in the presence of a reducing agent and in the absence of other carbon sources and separate physical electrolyte and electrodes, and conducting said contacting in the presence of light so that the energy of reduction is essentially supplied by said light.

2. The method according to claim 1 wherein said light is one of artificial light, sunlight, or a combination thereof.

3. The method according to claim 1 wherein said compounds are carbon monoxide, methanol, formaldehyde, methane, and formic acid.

4. The method according to claim 1 wherein said reducing agent is an aqueous carrier liquid.

5. The method according to claim 4 wherein said metal compound is dispersed in said carrier liquid and said carbon dioxide and/or bicarbonate ion is carried to said metal compound by said liquid.

6. The method according to claim 1 wherein said reducing agent is water.

7. The method according to claim 1 wherein said metal compound is in subdivided form.

8. The method according to claim 7 wherein said metal compound is subdivided into powder form.

9. The method according to claim 1 wherein said metal compound is heat treated prior to contact with carbon dioxide or the bicarbonate ion by heating at a temperature of from about 20° C. to about 600° C. for at least one hour in air, argon, hydrogen or a vacuum.

10. The method according to claim 9 wherein said heat treatment is for from about one hour to about forty-eight hours in air.

11. The method according to claim 9 wherein said heat treatment is for from about one hour to about forty-eight hours in a vacuum.

12. The method according to claim 9 wherein said heat treatment is for from about one hour to about forty-eight hours in argon or hydrogen.

13. The method according to claim 1 wherein said light has a wavelength range such that at least part of said light is absorbed by said metal compound.

14. The method according to claim 1 wherein said at least one compound is selected from the group consisting of carbon monoxide, alcohols, aldehydes, hydrocarbons, and carboxylic acids having 1 to 2 carbon atoms per molecule.

* * * * *